(12) United States Patent
Murakami

(10) Patent No.: US 8,382,743 B2
(45) Date of Patent: Feb. 26, 2013

(54) OPHTHALMIC LASER TREATMENT APPARATUS

(75) Inventor: Naho Murakami, Toyokawa (JP)

(73) Assignee: Nidek Co., Ltd., Gamagori-Shi (JP)

( * ) Notice: Subject to any disclaimer, the term of this patent is extended or adjusted under 35 U.S.C. 154(b) by 549 days.

(21) Appl. No.: 12/654,509

(22) Filed: Dec. 22, 2009

(65) Prior Publication Data

US 2010/0174273 A1    Jul. 8, 2010

(30) Foreign Application Priority Data

Jan. 7, 2009    (JP) ................... 2009-001357

(51) Int. Cl.
*A61B 18/18*    (2006.01)

(52) U.S. Cl. .................. 606/4; 606/10; 606/12

(58) Field of Classification Search ............... 606/4–6, 606/10–13, 16–19
See application file for complete search history.

(56) References Cited

U.S. PATENT DOCUMENTS

| | | | |
|---|---|---|---|
| 7,192,425 B2* | 3/2007 | Mizuno | 606/17 |
| 7,393,349 B2* | 7/2008 | Abe et al. | 606/4 |
| 8,066,696 B2* | 11/2011 | Abe | 606/4 |
| 2002/0103480 A1 | 8/2002 | Abe | |
| 2005/0288745 A1 | 12/2005 | Andersen et al. | |
| 2007/0129775 A1 | 6/2007 | Mordaunt et al. | |
| 2008/0243108 A1 | 10/2008 | Murakami et al. | |

FOREIGN PATENT DOCUMENTS

| | | |
|---|---|---|
| JP | A-2002-224154 | 8/2002 |
| JP | A-2008-504075 | 2/2008 |
| WO | WO 2007/035855 A2 | 3/2007 |

\* cited by examiner

*Primary Examiner* — Mohammed Hasan
(74) *Attorney, Agent, or Firm* — Oliff & Berridge, PLC

(57) ABSTRACT

An ophthalmic laser treatment apparatus for irradiating a laser beam to a patient's eye, comprises: a delivery optical system for forming the laser beam emitted from a laser source into a plurality of spots on a target surface, the delivery optical system including: a diffraction optical element for dividing the laser beam incident thereon into a plurality of diffraction beams in a predetermined spot pattern; a first zoom optical system placed on a side closer to the laser source than the diffraction optical element, the first zoom optical system being configured to change a spot size without changing a spot interval on the target surface; and an objective lens.

15 Claims, 6 Drawing Sheets

OPHTHALMIC LASER TREATMENT APPARATUS

CROSS-REFERENCE TO RELATED APPLICATIONS

This application is based upon and claims the benefit of priority from the prior Japanese Patent Application No. 2009-001357 filed on Jan. 7, 2009, the entire contents of which are incorporated herein by reference.

TECHNICAL FIELD

The present invention relates to an ophthalmic laser treatment apparatus for performing photocoagulation treatment or the like by irradiating a laser beam to a patient's eye.

BACKGROUND ART

A conventional laser treatment apparatus for performing photocoagulation treatment or the like by irradiating a laser beam to a fundus is configured to irradiate a laser beam as a single spot to an affected part of a patient's eye. For changing a spot position of the laser beam, an operator moves a delivery optical system for delivering the laser beam or moves a reflection mirror by operation of a manipulator to reflect the laser beam toward the eye (for example, see JP 2002-224154 A).

Furthermore, there has been proposed another apparatus using a scanner to cause a single spot of a laser beam scan in a predetermined pattern instead of moving the reflection mirror by the operator (for example, WO 2007/035855 A2 and JP 2008-504075 T2).

However, in the conventional apparatus in JP 2002-224154 A, in the case where a laser beam is to be irradiated to many affected parts, such as retinal photocoagulation, the operator has to move the delivery optical system or the reflection mirror every time an irradiation point of the laser beam is changed. This operation is troublesome and takes a long treatment time.

The apparatus utilizing the scanner can reduce the labor of the operator. However, this apparatus moves a single spot and therefore takes a long treatment time when a laser irradiation time at each spot position is set to be equal to that in JP 2002-224154 A. This results in an increased burden on a patient. If the laser irradiation time at each spot position is shortened and instead output power of the laser beam is increased, the following problems may be caused: operator's past experience could not be fully utilized and thus a coagulation spot could not be appropriately formed; the increased output power in a short irradiation time is liable to cause pain in a patient's eye; and bleeding easily occurs.

SUMMARY OF INVENTION

Technical Problem

The present invention has a purpose to provide an ophthalmic laser treatment apparatus capable of reducing the labor of an operator, shortening a treatment time, and performing treatment under an. irradiation condition making use of the operator's experience.

Solution to Problem

To achieve the above purpose, the invention provides an ophthalmic laser treatment apparatus for irradiating a laser beam to a patient's eye, comprising: a delivery optical system for forming the laser beam emitted from a laser source into a plurality of spots on a target surface, the delivery optical system including: a diffraction optical element for dividing the laser beam incident thereon into a plurality of diffraction beams in a predetermined spot pattern; a first zoom optical system placed on a side closer to the laser source than the diffraction optical element, the first zoom optical system being configured to change a spot size without changing a spot interval on the target surface; and an objective lens.

According to another aspect, the present invention provides an ophthalmic laser treatment apparatus for irradiating a laser beam to a patient's eye, comprising: a delivery optical system for forming the laser beam emitted from a laser source into a plurality of spots on a target surface, the delivery optical system including: a diffraction optical element for dividing the laser beam incident thereon into a plurality of diffraction beams in a predetermined spot pattern; a first zoom optical system placed on a side closer to the laser source than the diffraction element; a second zoom optical system placed on a side closer to the target surface than the diffraction element; and an objective lens.

DESCRIPTION OF EMBODIMENTS

Figure 1:
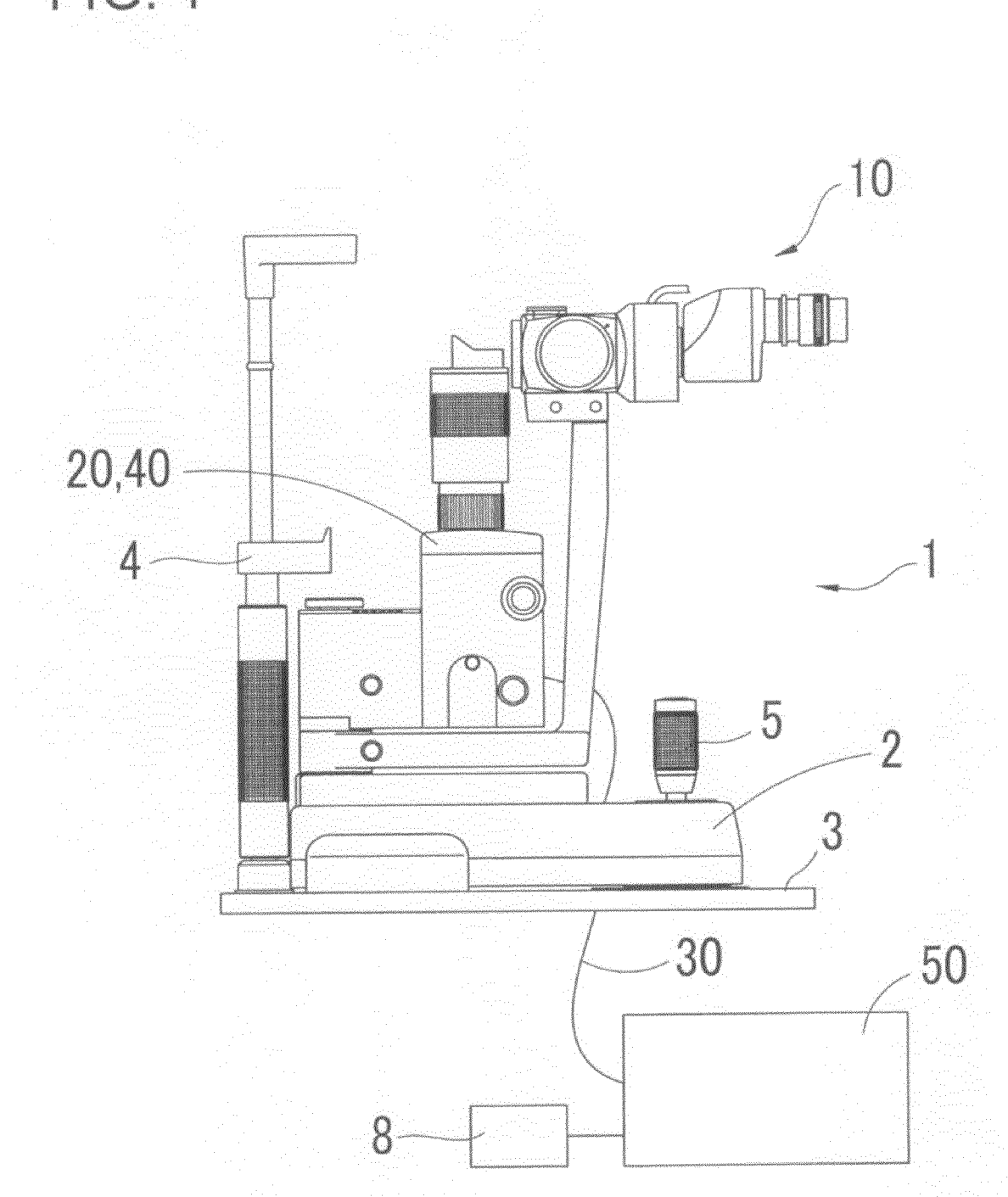
FIG. 1 is a schematic configuration view of an ophthalmic laser treatment apparatus.
Figure 2:
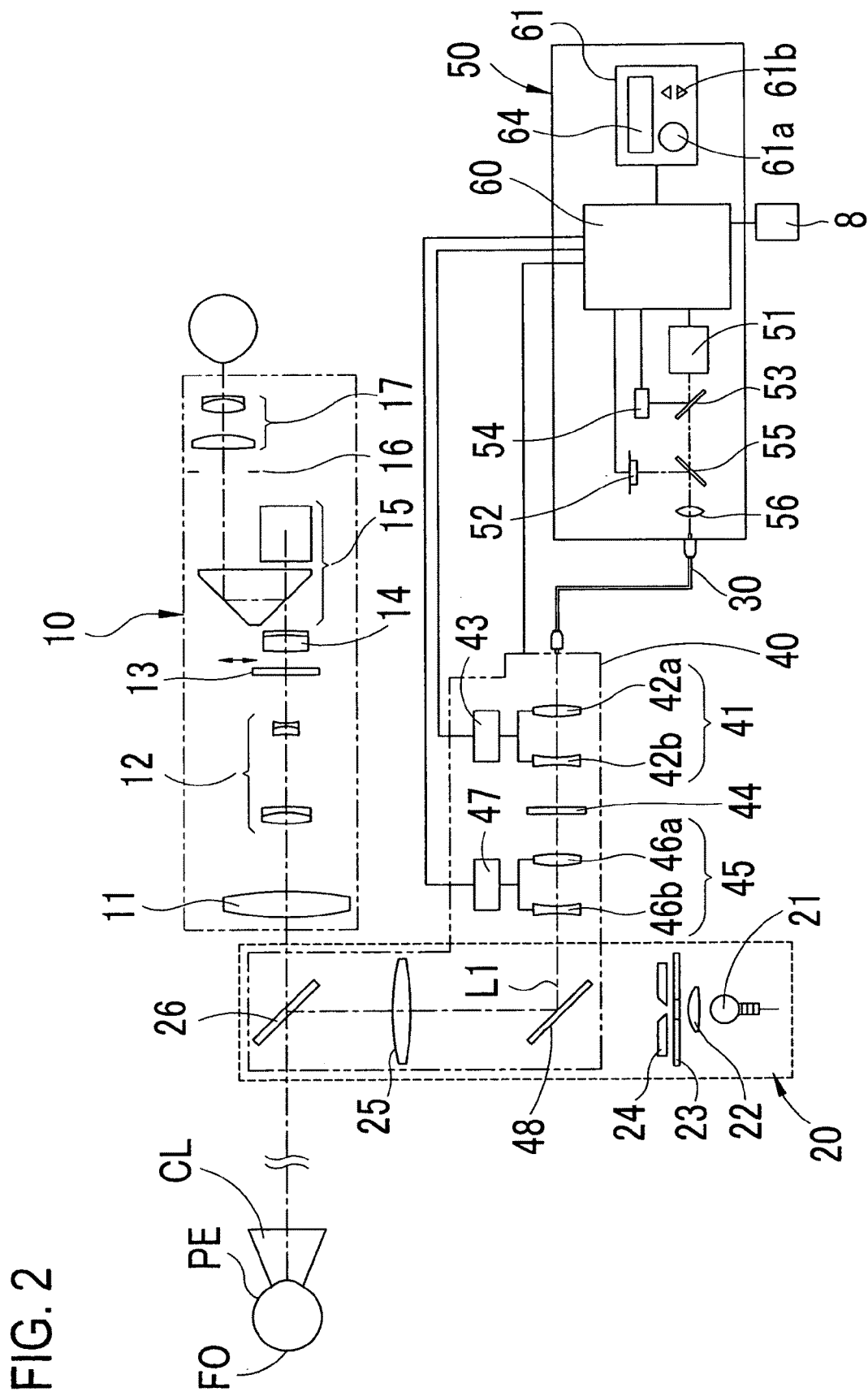
FIG. 2 is a configuration view of an optical system and a control system.

A detailed description of a preferred embodiment of the present invention will now be given referring to the accompanying drawings. FIG. 1 is a schematic configuration view of an ophthalmic laser treatment apparatus. FIG. 2 is a configuration view of an optical system and a control system.

The laser treatment apparatus includes a slit lamp 1 in which an observation optical system 10 for a binocular microscope and an illumination optical system 20 are placed, a main unit 50 containing a laser source, an optical fiber 30 for delivering a laser beam from the main unit 50, and a laser delivery optical system 40 for irradiating a laser beam emitted from the optical fiber 30 to an affected part such as a fundus of a patient's eye PE and others. The observation optical system 10, the illumination optical system 20, and the laser delivery optical system 40 are mounted on a movable base 2 which is movable on a table 3. The table 3 is provided with a chin rest 4 for supporting the face of a patient. The movable base 2 is moved with respect to the eye by a joystick 5 to be operated by an operator.

In FIG. 2, the observation optical system 10 includes an objective lens 11 to be used in common between right and left observation optical paths, a magnification lens unit 12, an operator protecting filter 13, an image forming lens 14, an erect prism 15, a field diaphragm 16, and an eyepiece 17, which are placed in each of the optical paths.

A visible light beam emitted from the illumination light source 21 of the illumination optical system 20 passes through a condenser lens 22, a variable aperture 23 for determining the height of the beam, and a variable slit plate 24 for determining the width of the beam. Thus, the beam is formed into a slit-like beam. This slit illumination light passing through the variable slit plate 24 passes through a projection lens 25 and then is reflected by a mirror 26 to illuminate the patient's eye PE. In the case of fundus observation and fundus photocoagulation, a contact lens CL for canceling a corneal refraction power is used.

The main unit 50 includes a treatment laser source 51 and an aiming laser source 52 such as a semiconductor laser to generate a red aiming beam. The laser source 51 emits a laser beam having a visible wavelength (e.g., a wavelength of 532 nm) suitable for photocoagulation treatment. The laser beam emitted from the laser source 51 is partly reflected by a beam splitter 53 and the output of the laser beam is monitored by an output sensor 54. The laser beam passing through the beam splitter 53 is made coaxial with the aiming beam from the aiming laser source 52 and caused to enter the optical fiber 30 through a condensing lens 56.

The laser beam and the aiming beam emitted from the main unit 50 are transmitted to the laser delivery optical system 40 through the fiber 30. The fiber 30 used in this embodiment shown in FIG. 2 has a core diameter of 50 μm.

The laser delivery optical system 40 includes a diffractive optical element (hereinafter, "DOE") 44 for forming a plurality of spots in a predetermined pattern on a target surface FO (the fundus). On both sides of the DOE 44, a first zoom optical system 41 is placed on a side closer to the laser source 51 which is an incident side of the DOE 44 and a second zoom optical system 45 is placed on a side closer to the target surface FO which is an emission side of the DOE 44. The laser beam (and the aiming beam) passing through the second zoom optical system 45 is reflected by a dichroic mirror 48 disposed on an illumination optical axis of the illumination optical system 20 toward the eye PE through the projection lens 25 and the mirror 26 used in common with the illumination optical system 20. The laser delivery optical system 40 uses the projection lens 25 as an objective lens. Furthermore, an emission end face of the fiber 30 is conjugated with the target surface FO with respect to the lens 25. The dichroic mirror 48 has a property of reflecting most of the laser beam from the laser source 51, reflecting a certain amount of the red aiming beam, and transmitting a certain amount of white light from the illumination light source 21.

The first zoom optical system 41 includes a convex lens 42a and a concave lens 42b movable in an optical axis direction. The convex lens 42a serves as a variator lens (serves to change the size of an image). Movement of the convex lens 42a changes the size of spots to be formed on the target surface FO. The concave lens 42b serves as a compensator lens (movable synchronously with the variator lens and serves to compensate deviation of a focal point on the target surface FO). The concave lens 42b is moved in the optical axis direction synchronously with the convex lens 41a in order to cause almost parallel light to enter the DOE 44. The convex lens 42a and the concave lens 42b are moved in the optical axis direction synchronously with a drive unit 43 having a motor and a moving mechanism. For the lenses 42a and 42b, a known cam mechanism for zoom lens barrel utilizable in a photographic camera and others may be used. The use of such cam mechanism enables synchronous movement of the convex lens 42a and the 42b by manual operation.

The second zoom optical system 45 includes a convex lens 46a and a concave lens 46b which will be moved in the optical axis direction. The parallel light passing through the first zoom optical system 41 is incident on the convex lens 46a, forming a magnified image of an emission end face (core) of the fiber 30 serving as a subject plane on a focal plane of the convex lens 46a. In the configuration that the DOE 44 is placed between the first zoom optical system 41 and the second zoom optical system 45, multiple spots are formed on the focal plane of the convex lens 46a according to a diffraction angle of the DOE 44. The concave lens 46b serves to magnify the spots formed on the focal plane of the convex lens 46a by the DOE 44 and the convex lens 42a. The convex lens 46a is moved synchronously with the concave lens 46b to focus on the target surface FO. In the second zoom optical system 45, the convex lens 46a functions as a compensator lens and the concave lens 46b functions as a variator lens. The convex lens 46a and the concave lens 46b are synchronously moved in the optical axis direction by a drive unit 47 having a motor and a moving mechanism. For the lenses 46a and 46b, a known cam mechanism for zoom lens barrel may be used as in the first zoom optical system 41. The second zoom optical system 45 may also be configured to move each constituent lens by manual operation instead of using the drive unit 47.

Figure 5A:
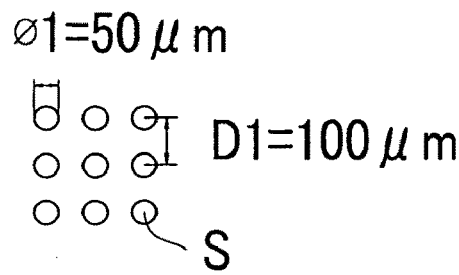
FIGS. 5A to 5C are explanatory views showing the case of changing spot intervals without changing a spot size.

The DOE 44 is an optical element formed of a light-transmitting body, such as glass, quartz, or resin, formed with microgrooves for generating diffraction. The microgrooves of the DOE 44 can give a diffraction phenomenon of an arbitral pattern to the light passing through the DOE 44. The DOE 44 in this embodiment is designed to divide a laser beam incident thereon into a plurality of diffraction beams in a predetermined spot pattern and form a plurality of spots (multiple spots) having the same shape and arranged in the predetermined pattern on the target surface. For instance, as shown in FIG. 5A, the DOE 44 is designed to divide the diffraction light to form nine circular spots arranged at equal intervals in a grid pattern on the focal surface of the convex lens 46a. Furthermore, the DOE 44 is also designed so that, when the fiber 30 used herein has a core diameter of 50 μm and the magnifications to be changed by the first zoom optical system 41 and the second zoom optical system 45 respectively are 1, each spot on the target surface FO is 50 μm in diameter and each distance between the centers of the spots is 100 μm. Moreover, the DOE 44 is designed to have a property that the multiple spots are almost equal in spot size and energy intensity. In the DOE 44, the shape of one spot may be freely designed to be rectangular, hexagonal, or others as well as circular.

A control section 60 installed in the main unit 50 is connected to the laser source 51, the aiming laser source 52, the output sensor 54, the drive units 43 and 47, a footswitch 8 for inputting a trigger signal of laser irradiation, a controller 61, and others. The control section 60 controls output power of the laser beam, duration of the laser beam, and switching ON/OFF of the aiming beam. The controller 61 is provided with a switch 61a for changing the spot size of the laser beam, a switch 61b for setting an irradiation range of the laser beam (the total dimension of the multiple spots), and further various switches such as a switch for setting surgical parameters such as the output power (an energy amount) and irradiation time of the laser beam, and a switch for adjusting an illumination light amount. The controller 61 is provided with a display (an indicator) 64 for indicating surgical conditions set with the switches. The control section 60 controls driving of the drive units 43 and 47 to change the emission condition, the spot size, etc. of the laser beam from the laser source 51 based on the parameters set by the controller 61.

Figure 3:
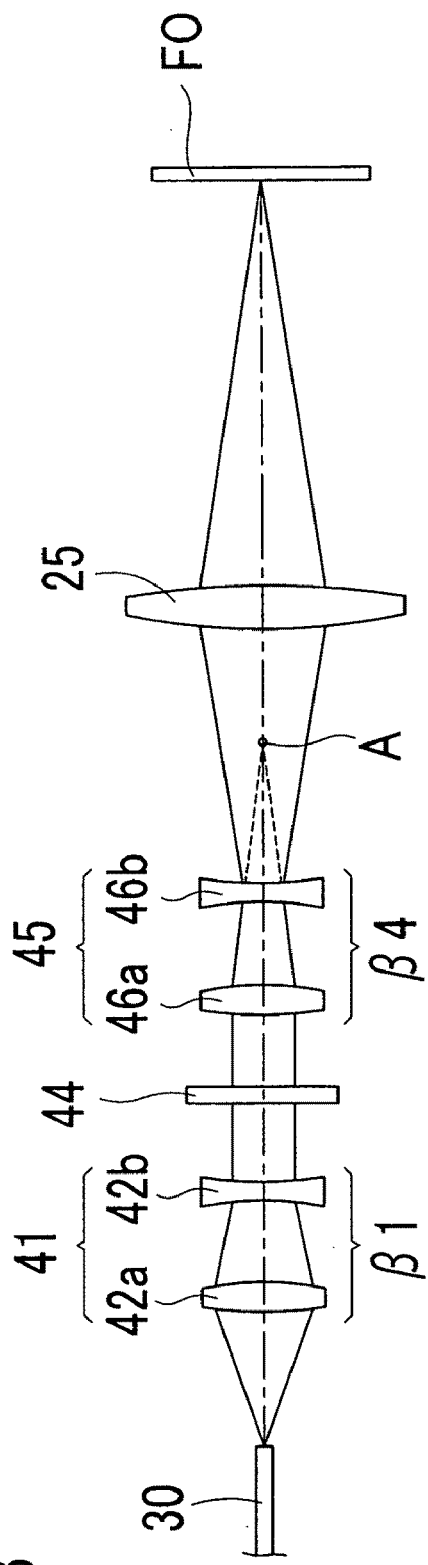
FIG. 3 is a configuration view of major optical members of a laser delivery optical system.

Next, the principle of changing the size and the irradiation range of the spots to be irradiated on the target surface is explained. FIG. 3 is a configuration view of major optical members of the laser delivery optical system 40. In FIG. 3, it is assumed that a magnification to be changed by the first zoom optical system 41 (i.e., the magnification to be changed by movement of the convex lens 42a) is $\beta1$, a magnification to be changed by the second zoom optical system 45 (i.e., the magnification to be changed by movement of the concave lens 46b) is $\beta4$, a focal distance of the concave lens 42b is f2 (not shown), and a focal distance of the convex lens 46a is f3. Herein, when the magnification $\beta4$ obtained by the second zoom optical system 45 is 1, a magnification M of the spot size formed on the target surface FO and the magnification $\beta1$ obtained by the first zoom optical system 41 have the following relation. In the following expression, C represents a magnification (a constant number) to be determined by the projection lens 25.

$$M = \beta1 \times \frac{f3}{f2} \times C \quad \text{[Expression 1]}$$

Diffraction beams divided by the DOE 44 form for example nine spots S having the same size and the same shape as shown in FIG. 5A on the target surface. At that time, the focal distance f2 of the concave lens 42b and the focal distance f3 of the convex lens 46a are fixed. Accordingly, the magnification M of each spot S is determined by the magnification $\beta1$ obtained by the first zoom optical system 41. In the case where the magnification $\beta4$ by the second zoom optical system 45 is changed, the magnification M of each spot S is calculated by the following expression.

$$M = \beta1 \times \frac{f3}{f2} \times \beta4 \times C \quad \text{[Expression 2]}$$

In other words, when the magnification $\beta4$ by the second zoom optical system 45 is changed, the magnification M of each spot S is determined based on both of the magnification $\beta1$ by the first zoom optical system 41 and the magnification $\beta4$ by the second zoom optical system 45. For instance, in the case where the spot size of each spot S remains unchanged and only the total irradiation range is to be changed, the magnification $\beta1$ by the first zoom optical system 41 is adjusted according to the magnification $\beta4$ by the second zoom optical system 45 so that the magnification M of each spot S is constant.

Figure 4:
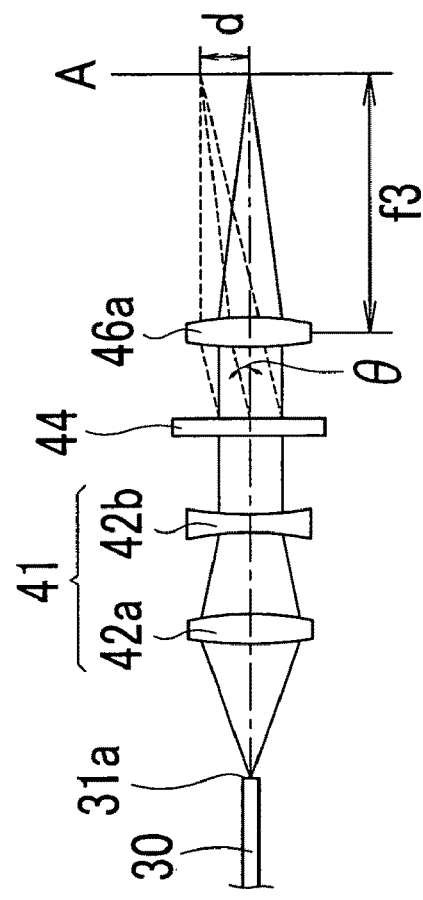
FIG. 4 is an explanatory view showing a distance between a spot formed on a focal plane and an optical axis.

As shown in FIG. 4, the convex lens 46a forms a magnified image of the emission end face 31a of the fiber 30, which is a light source image, on a focal plane A of the convex lens 46a. When the DOE 44 is placed between the concave lens 42b and the convex lens 46a, a plurality of spots are formed on the focal plane A of the convex lens 46a according to the diffraction angles of the DOE 44. If one diffraction angle of the DOE 44 is $\theta$, a distance "d" of one spot formed on the focal plane A at a diffraction angle $\theta$ from the optical axis L1 is expressed by:

$$d = f3 \times \tan\theta \quad \text{[Expression 3]}$$

Since the DOE 44 is designed to have a plurality of diffraction angles $\theta$, a plurality of spots are formed on the focal plane A according to the diffraction angles $\theta$.

The convex lens 46a of the second zoom optical system 45 serves to magnify the multiple spots formed on the focal plane A of the convex lens 46a. The convex lens 46a is moved synchronously with the concave lens 46b to focus on the target surface FO. When each interval between the spots formed on the focal plane A of the convex lens 46a is "d", each interval "D" of the spots on the target surface FO and the magnification $\beta4$ by the second zoom optical system 45 have the following relation.

$$D = d \times \beta4 \quad \text{[Expression 4]}$$

Specifically, the interval D is determined based on the magnification $\beta4$ by the second zoom optical system 45.

Figure 5B:
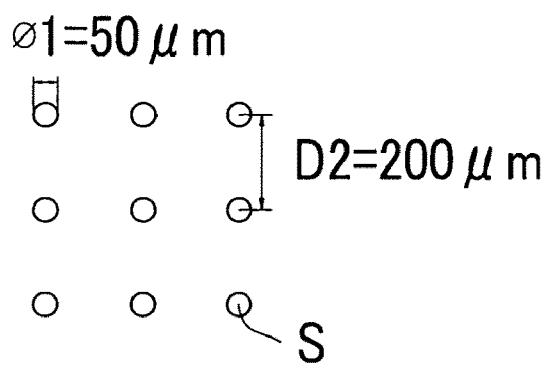
Figure 5C:
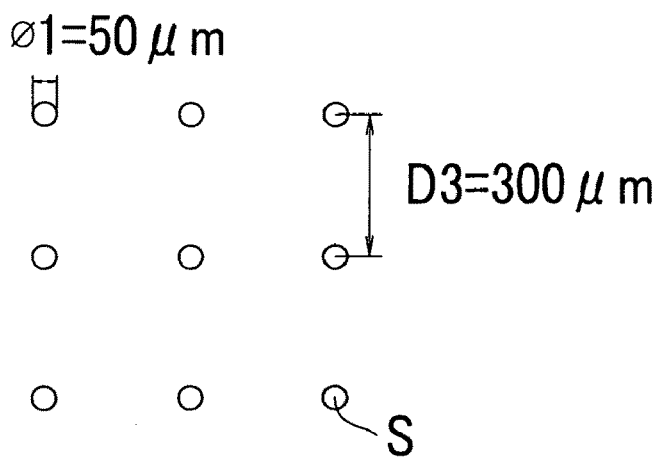

FIGS. 5a to 5C are explanatory views showing the case of changing only the spot interval D without changing the spot size $\phi$ on the target surface FO. FIG. 5A shows nine spots formed on the target surface FO. For example, for the magnification $\beta1=1$ and the magnification $\beta4=1$, it is assumed that the spot size $\phi$ is $\phi1=50$ μm and the equal spot interval D is D1=100 μm.

FIG. 5B shows the case where the spot size $\phi1$ remains 50 μm and the spot interval D is changed to D2=200 μm, double D1 in FIG. 5A. In this case, the magnification $\beta4$ of the second zoom optical system 45 is increased (doubled) and thus the spot interval D is also magnified (doubled) from that in FIG. 5A. However, when the magnification $\beta4$ is increased, the spot size $\phi$ of each spot S is also magnified. Therefore, the magnification $\beta1$ by the first zoom optical system 41 is adjusted to keep the magnification M of the spot size $\phi$ constant. In this example, specifically, the magnification $\beta4$ is set to 2 and the magnification $\beta1$ is adjusted to 0.5.

FIG. 5C shows the case where the spot size $\phi1$ remains 50 μm and the spot interval D is changed to D3=300 μm, triple D1 in FIG. 5A. In this case, the magnification $\beta4$ is set to 3 and the magnification $\beta1$ is adjusted to ⅓.

As in the above examples in which the spot size $\phi$ is constant and only the spot interval D is changed, the magnification $\beta4$ by the second zoom optical system 45 is changed according to magnification (reduction) of the spot interval D. Also, the magnification $\beta1$ by the first zoom optical system 41 is changed according to the magnification $\beta4$ to make the magnification M of each spot size $\phi$ constant.

Figure 6A:
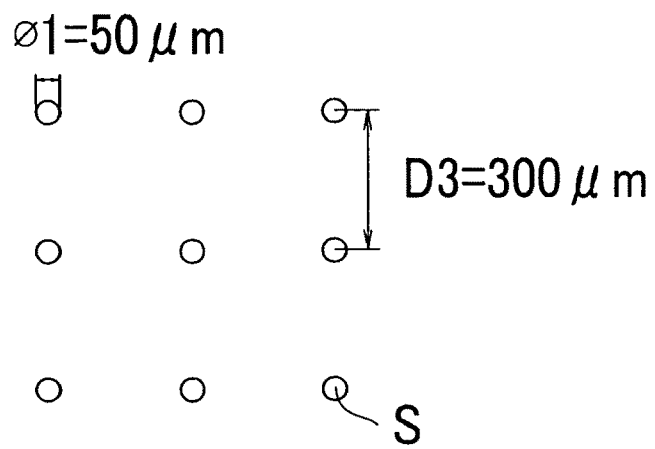
FIGS. 6A to 6C are explanatory views showing the case of changing the spot size without changing the spot intervals.
Figure 6B:
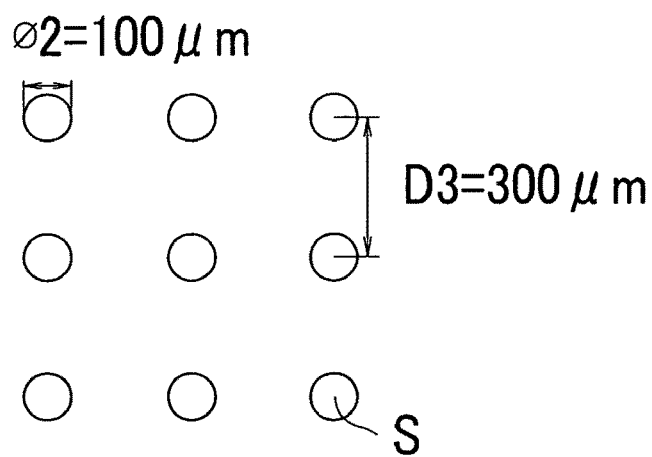
Figure 6C:
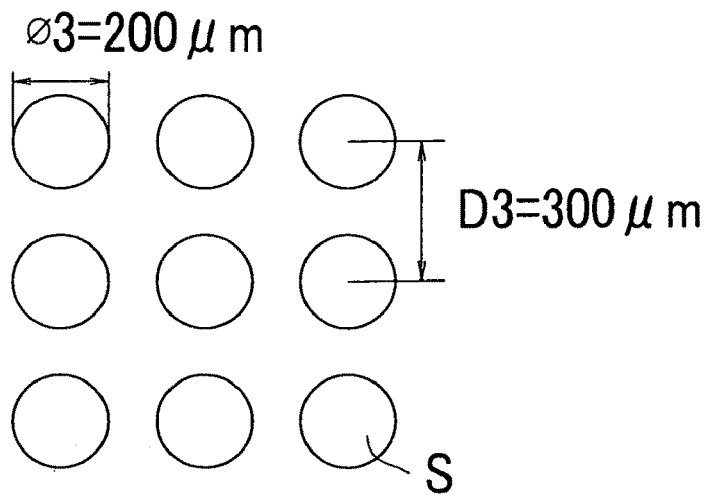

FIGS. 6A to 6C are explanatory views showing the case of changing the spot size $\phi$ without changing the spot interval D formed on the target surface FO. FIG. 6A shows, as with FIG. 5C, the case where the spot size $\phi$ is $\phi1=50$ μm and the spot size D is D3=300 μm. In this case, the magnification $\beta1$ is ⅓ and the magnification $\beta4$ is 3.

FIG. 6B shows the case where the spot interval D remains D3=300 μm and the spot size $\phi$ is changed to $\phi2=100$ μm. In this case, the magnification $\beta1$ by the first zoom optical system 41 is set to ⅔ to double the spot size $\phi1$ in FIG. 6A, and the magnification $\beta4$ by the second zoom optical system 45 is maintained to be 3 as in FIG. 6A. FIG. 6C shows the case where the spot interval D is maintained to be D3=300 μm and the spot size $\phi$ is changed to $\phi3=200$ μm. In this case, the magnification $\beta1$ by the first zoom optical system 41 is set to $\beta1=4/3$ to quadruple the spot size $\phi1$ in FIG. 6A and the magnification $\beta4$ by the second zoom optical system 45 is maintained to be $\beta4=3$ as in FIG. 6A.

As the above examples, when the sport interval D is fixed and only the spot size $\phi$ is changed, the magnification $\beta4$ is not changed and only the magnification $\beta1$ is changed. When the spot size $\phi$ is to be displayed on the display (the indicator) 64, the spot size $\phi$ is calculated by the control section 60 based on the magnifications $\beta1$ and $\beta4$.

Operations of the laser treatment apparatus during surgical operation will be explained below. Herein, the explanation is given to the case of performing photocoagulation treatment on a fundus. For photocoagulation treatment, an operator determines the irradiation time, the output power, and others of the laser beam with various switches not shown on the controller 61. The irradiation time and the output power are also displayed on the display 64. The laser output power displayed on the display 64 appears as a value of total laser output power and also as a value of output power per one spot so as to make use of operator's experience. For instance, when the laser output power at one spot is set to 0.1 W, the control section 60 drives the laser source 51 to output laser power at 0.9 W in total based on the number of diffraction beams divided by the DOE 44 (the number of spots is set to 9).

The operator further sets the spot size $\phi$ with the switch $61a$ for spot size change and also sets the spot interval D (which also may be set as a range of nine spots S corresponding to the irradiation range of the laser beam) with the switch $61b$. The spot size $\phi$ and the spot interval D are displayed on the display 64. When the spot interval D is set, the control section 60 determines the magnification $\beta 4$ based on a set signal representing the spot interval D, and controls the drive unit 47 to drive the second zoom optical system 45. The control section 60 also determines the magnification $\beta 1$ by the first zoom optical system 41 based on drive information (the magnification $\beta 4$) of the second zoom optical system 45 and the set signal representing the spot size $\phi$, and controls the drive unit 43 to drive the first zoom optical system 41 to adjust the spot size $\phi$ to the set value. For instance, under the above conditions in FIGS. 5 and 6, the magnification $\beta 4$ by the second zoom optical system 45 is set to 3 for the spot interval D of 300 μm and the magnification $\beta 1$ by the first zoom optical system 41 is determined to be 4/3 for the spot size $\phi$ of 200 μm.

The operator observes, through the observation optical system 10, an affected part of the fundus illuminated by illumination light from the illumination optical system 20. When the aiming laser source 52 is turned on, the aiming beam from the aiming laser source 52 is guided into the laser delivery optical system 40 through the fiber 30, and passes through the first zoom optical system 41, the DOE 44, the second zoom optical system 45, and the projection lens 25, thereby forming nine spots as illustrated in FIG. 5A. The aiming beam is made coaxial with the laser beam and thus irradiated to the fundus at the spot size and the spot interval set by the controller 61. While observing the nine spots of the aiming beam irradiated to the fundus, the operator manipulates the joystick 5 and others to move the slit lamp 1 and the laser delivery optical system 40 to align the aiming beam with the affected part. When the intervals D between the nine spots are changed by observation of the multiple spots of the aiming beam irradiated to the affected part, the operator operates the switch $61b$. The controller 60 determines the magnification $\beta 4$ by the second zoom optical system 45 according to the changed spot interval D and moves the convex lens $46a$ and the concave lens $46b$, and also determines the magnification $\beta 1$ by the first zoom optical system 41 according to the magnification $\beta 4$ to maintain the spot size $\phi$ at the set value, and moves the convex lens $42a$ and the concave lens $42b$.

When the operator makes alignment to the affected part while observing the nine spots formed by the aiming beam, the operator performs laser irradiation by use of the footswitch 8. Upon receipt of the trigger signal of the laser irradiation from the footswitch 8, the control section 60 drives the laser source 51 to emit the laser beam. The laser beam from the laser source 51 is guided into the delivery optical system 40 through the optical fiber 30 and passes through the first zoom optical system 41, the DOE 44, the second zoom optical system 45, and the objection lens 25. Thus, the laser beams divided into nine spots are irradiated at once to the fundus for the set irradiation time. Consequently, nine coagulation spots are simultaneously formed. In treatment for forming many coagulation spots as in retinal photocoagulation treatment, the laser beams of nine spots are irradiated at once to the fundus. This can save the operator time and labor for alignment and shorten the treatment time. Since the treatment is enabled under the same irradiation time and laser output power as in the laser irradiation performed individually for each spot. Thus, the treatment can be conducted appropriately based on the operator's experience.

The above embodiment exhibits the example of using the DOE 44 to form the patterns in which nine spots are arranged in a grid form. An alternative is to provide a plurality of DOEs configured to form different arrangement patterns of multiple spots to enable selection of a multi-spot irradiation pattern, so that more appropriate treatment is performed according to conditions of the affected part.

Figure 7:
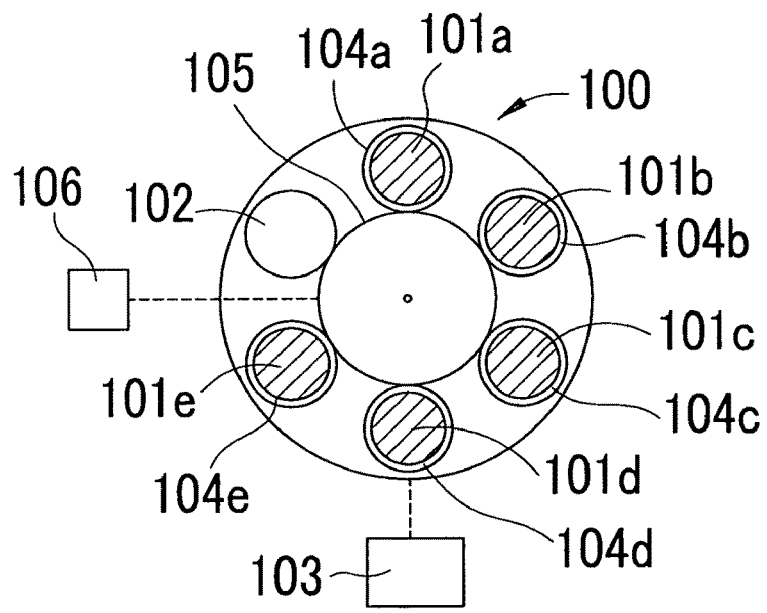
FIG. 7 shows an example of a configuration for selecting an arrangement pattern of multiple spots.

FIG. 7 shows an examination of a configuration of a changing mechanism for selectively changing the multi-spot arrangement patterns. On a turret plate 100, DOEs $101a$, $101b$, $101c$, $101d$, $101e$ for forming different multi-spot patterns and an opening 102 are arranged on the same circle. Instead of the DOE 44 in FIG. 2, the turret plate 100 is rotated by a rotating unit 103 constituted of a motor and others to place one of the DOEs $101a$ to $101e$ and the opening 102 onto an optical path between the first zoom optical system 41 and the second zoom optical system 45 in the laser delivery optical system 40. The rotating unit 103 is driven by the control section 60 based on a signal from a selection switch provided on the controller 61. The turret plate 100 may be manually rotated by the operator to select a desired one of the DOEs $101a$ to $101e$.

The DOEs $101a$ to $101e$ are rotatably held in the turret plate 100 by holders $104a$ to $104e$ respectively. Each of the holders $104a$ to $104e$ is rotated synchronously with rotation of a sun gear 105 by the motor 106. When one of the DOEs $101a$ to $101e$ placed on the optical axis of the laser delivery optical system 40 is rotated about the optical axis, the multi-spot pattern to be irradiated to the eye PE is also rotated. The motor 106 is driven by the control section 60 based on a signal from a rotation-angle designating switch provided on the controller 61. The rotation of each of the DOEs $101a$ to $101e$ about the optical axis may also be performed by manual rotation of each DOE or the sun gear 105 by the operator to rotate the multi-spot pattern.

Figure 8A:
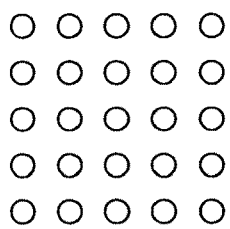
FIGS. 8A to 8E show examples of patterns of multiple spots.
Figure 8B:
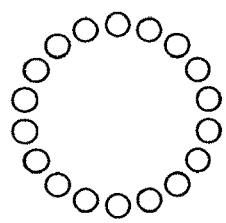
Figure 8C:
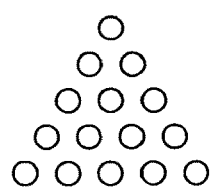
Figure 8D:
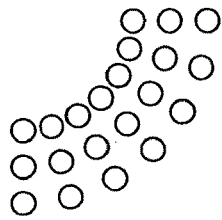
Figure 8E:

FIGS. 8A to 8E show examples of the multi-spot patterns to be formed by the DOEs $101a$ to $101e$, respectively. FIG. 8A shows a pattern of multiple spots arranged in a grid form. FIG. 8B shows a pattern of multiple spots arranged in a circular form. FIG. 8C shows a pattern of multiple spots arranged in a triangular form. FIG. 8D shows a pattern of multiple spots arranged in a fan-like form. FIG. 8E shows a pattern of multiple spots arranged in a linear form. The circular pattern in FIG. 8B is suitable, for example, for the case of entirely photocoagulating the portions surrounding a macula without irradiating the macula. The fan-like pattern in FIG. 8D is suitable for the case of partly photocoagulating the portions surrounding a macula. As the DOE $101d$ is rotated about the optical axis, the fan-like pattern is also rotated in any direction. The triangular pattern in FIG. 8C and the linear pattern in FIG. 8E are similarly rotated by rotation of the corresponding DOEs $101c$ and $101e$ about the optical axis.

When the opening 102 is placed on the optical path (that is, when the DOEs are placed out of the optical path), the laser beam from the laser delivery optical system 40 is formed in a single spot. This enables treatment using a single spot as with the conventional apparatus. The aforementioned configuration having the DOE 44 in FIG. 2 also may be arranged to selectively move the DOE 44 in or out of the optical path by a moving mechanism, thereby enabling selection of a single spot. The moving mechanism in this case is constituted of the turret plate 100 and the rotating unit 103. After the DOE 44 is moved out of the optical path, the spot size of the single spot can be changed by the first zoom optical system 41.

In the above method, when the spot diameter and the irradiation range are to be changed, the first zoom optical system 41 and the second zoom optical system 45 are electrically driven. Alternatively, the first and second zoom optical systems 41 and 45 may be moved by manual operation of a rotating knob or the like by the operator. In this case, a sensor is preferably provided to detect a movement position of each lens of the first and second zoom optical systems 41 and 45 or an operation position of the rotating knob. Accordingly, the magnifications by the first and second zoom optical systems 41 and 45 respectively are detected. Based on the detected magnifications, information on the spot size φ and the spot interval D (or the irradiation range) are displayed on the display 64. This enables the operator to perform appropriate laser irradiation while observing the spot size φ and the spot interval D.

In the embodiment of FIG. 2, the laser beam from the laser source 51 is guided into the laser delivery optical system 40 through the fiber 30. As an alternative, it may be arranged to guide the laser beam from the laser source 51 without passing through the fiber 30. In this case, instead of the emission end face of the fiber 30, the focal plane relayed by the laser source 51 or the lens and others is a subject plane of the first zoom optical system 41.

While the above embodiment of the present invention has been shown and described, it is to be understood that this disclosure is for the purpose of illustration and that various changes and modifications may be made without departing from the scope of the invention as set forth in the appended claims.

The invention claimed is:

1. An ophthalmic laser treatment apparatus for irradiating a laser beam to a patient's eye, comprising:
a delivery optical system for forming the laser beam emitted from a laser source into a plurality of spots on a target surface, the delivery optical system including:
a diffraction optical element for dividing the laser beam incident thereon into a plurality of diffraction beams in a predetermined spot pattern;
a first zoom optical system placed on a side closer to the laser source than the diffraction optical element, the first zoom optical system being configured to change a spot size without changing a spot interval on the target surface; and
an objective lens.

2. The ophthalmic laser treatment apparatus according to claim 1, wherein the delivery optical system includes a plurality of diffraction optical elements having different spot patterns from each other, the diffraction optical elements being selectively inserted in an optical path of the delivery optical system.

3. The ophthalmic laser treatment apparatus according to claim 2, wherein the plurality of diffraction optical elements are arranged on a turret plate, and
the apparatus further includes a drive unit for rotating the turret plate.

4. The ophthalmic laser treatment apparatus according to claim 1, wherein the delivery optical system further includes an optical fiber for guiding the laser beam from the laser source, and
the target surface and an emission face of the optical fiber are conjugated with respect to the objective lens.

5. The ophthalmic laser treatment apparatus according to claim 1, wherein the delivery optical system further includes a second zoom optical system placed on a side closer to the target surface than the diffraction optical element,
the second zoom optical system is configured to change a projection magnification of the spots on the target surface.

6. An ophthalmic laser treatment apparatus for irradiating a laser beam to a patient's eye, comprising:
a delivery optical system for forming the laser beam emitted from a laser source into a plurality of spots on a target surface, the delivery optical system including:
a diffraction optical element for dividing the laser beam incident thereon into a plurality of diffraction beams in a predetermined spot pattern;
a first zoom optical system placed on a side closer to the laser source than the diffraction element;
a second zoom optical system placed on a side closer to the target surface than the diffraction element; and
an objective lens.

7. The ophthalmic laser treatment apparatus according to claim 6 further including an input unit for inputting data on a spot size and a spot interval, the first zoom optical system and the second zoom optical system being driven based on the input data.

8. The ophthalmic laser treatment apparatus according to claim 6, wherein the first zoom optical system includes a first variator lens and a first compensator lens synchronously movable with each other to change a spot size without changing a spot interval; and
the second zoom optical system includes a second variator lens and a second compensator lens synchronously movable with each other to change the spot size and the spot interval.

9. The ophthalmic laser treatment apparatus according to claim 6, wherein the delivery optical system further includes an optical fiber for guiding the laser beam from the laser source,
the first zoom optical system includes: a first variator lens for changing a size of an image of an emission face of the optical fiber; and a first compensator lens movable synchronously with the first variator lens to cause almost parallel beam to enter the diffraction optical element; and
the second zoom optical system includes: a second compensator lens for forming the spots by the laser beam emitted from the diffraction optical element onto a focal plane of the second compensator lens; and a second variator lens movable synchronously with the second compensator lens to change a total size of the spots formed by the second compensator lens.

10. The ophthalmic laser treatment apparatus according to claim 6 further including:
a calculation unit for calculating a spot size to be formed on the target surface based on a magnification to be changed by the first zoom optical system and a magnification to be changed by the second zoom optical system; and
an indicator for indicating the calculated spot size.

11. The ophthalmic laser treatment apparatus according to claim 6 further including:

an input unit having a switch for inputting a first setting signal for setting a spot size and a second setting signal for setting a spot interval; and a control unit for controlling driving of the second zoom optical system based on the second setting signal and controlling driving of the first zoom optical system based on drive information of the second zoom optical system and the first setting signal.

12. The ophthalmic laser treatment apparatus according to claim 6 further comprising a moving mechanism for moving the diffraction optical element in and out of an optical path between the first zoom optical system and the second zoom optical system.

13. The ophthalmic laser treatment apparatus according to claim 6, wherein the diffraction optical element includes a plurality of diffraction optical elements having different spot patterns from each other.

14. The ophthalmic laser treatment apparatus according to claim 6, wherein the diffraction optical element is placed rotatably about an optical axis of the delivery optical system.

15. The ophthalmic laser treatment apparatus according to claim 6, wherein the diffraction optical element is designed to form the spots having the same shape and almost the same energy intensity.

* * * * *